United States Patent
Gharpure et al.

(10) Patent No.: US 11,312,740 B2
(45) Date of Patent: Apr. 26, 2022

(54) PROCESS FOR THE PREPARATION OF SGLT2 INHIBITORS AND INTERMEDIATES THEREOF

(71) Applicant: PIRAMAL PHARMA LIMITED, Maharashtra (IN)

(72) Inventors: Milind Gharpure, Maharashtra (IN); Sanjay Kumar Sharma, Maharashtra (IN); Sandesh Vishwasrao, Maharashtra (IN); Prasad Vichare, Maharashtra (IN); Dipak Varal, Maharashtra (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 12 days.

(21) Appl. No.: 16/611,558

(22) PCT Filed: May 9, 2018

(86) PCT No.: PCT/IB2018/053220
§ 371 (c)(1),
(2) Date: Nov. 7, 2019

(87) PCT Pub. No.: WO2018/207111
PCT Pub. Date: Nov. 15, 2018

(65) Prior Publication Data
US 2021/0147461 A1    May 20, 2021

(30) Foreign Application Priority Data
May 9, 2017   (IN) .............................. 201721016263

(51) Int. Cl.
C07H 7/04 (2006.01)
C07H 1/00 (2006.01)
C07H 1/06 (2006.01)
C07H 7/06 (2006.01)

(52) U.S. Cl.
CPC ................ C07H 7/04 (2013.01); C07H 1/00 (2013.01); C07H 1/06 (2013.01); C07H 7/06 (2013.01)

(58) Field of Classification Search
CPC ... C07H 1/00; C07H 1/06; C07H 7/04; C07H 7/06
See application file for complete search history.

(56) References Cited

U.S. PATENT DOCUMENTS

| 6,515,117 B2 | 2/2003 | Ellsworth et al. |
| 7,579,449 B2 | 8/2009 | Eckhardt et al. |
| 7,772,407 B2 | 8/2010 | Imamura et al. |
| 7,943,788 B2 | 5/2011 | Nomura et al. |

FOREIGN PATENT DOCUMENTS

| WO | 2003/099836 A1 | 12/2003 |
| WO | 2004/063209 A2 | 7/2004 |
| WO | 2008/075736 A1 | 6/2008 |
| WO | 2009/035969 A1 | 3/2009 |
| WO | 2010/022313 A2 | 2/2010 |
| WO | 2010/043682 A2 | 4/2010 |
| WO | 2011/047113 A2 | 4/2011 |
| WO | 2013/152476 A1 | 10/2013 |
| WO | 2015/155739 A1 | 10/2015 |
| WO | 2017/064679 A1 | 4/2017 |
| WO | 2017/141202 A1 | 8/2017 |

OTHER PUBLICATIONS

ISR for International Application No. PCT/IB2018/053220.
Writien Opinion for International Application No. PCT/IB2018/053220.

*Primary Examiner* — Jonathan S Lau
(74) *Attorney, Agent, or Firm* — Ladas & Parry LLP

(57) ABSTRACT

The present invention relates to an industrially feasible and economically viable process for preparation of SGLT2 inhibitors of formula X in significantly high yield and purity.

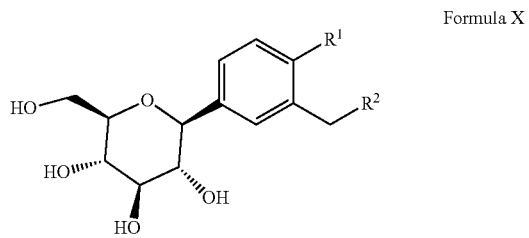

Formula X

6 Claims, No Drawings

PROCESS FOR THE PREPARATION OF SGLT2 INHIBITORS AND INTERMEDIATES THEREOF

RELATED APPLICATION

This application is an application under 35 U.S.C. 371 of International Application No. PCT/IB2018/053220 filed on 9 May 2018, which claims priority from Indian Application No, 201721016263 filed 9 May 2017, the disclosures of which are incorporated in their entirety by reference herein.

FIELD OF THE INVENTION

The present invention relates to a novel process for preparing sodium glucose transporters 2 (SGLT2) inhibitor compounds of Formula X.

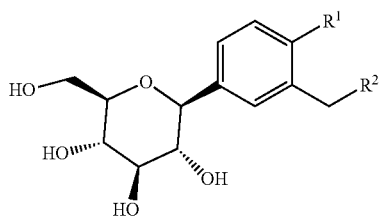

Formula X

Wherein, is halogen, alkyl or alkoxy group; and
$R_2$ is aryl group or heterocyclic ring selected from the group of i, ii, iii or iv as given below.

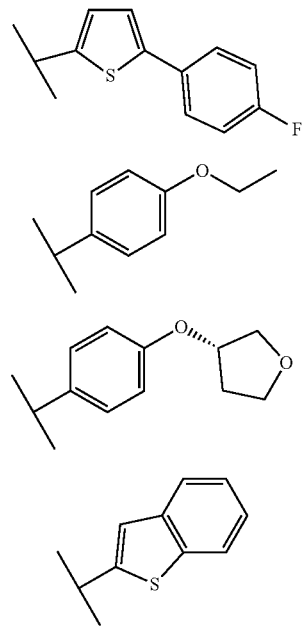

BACKGROUND OF THE INVENTION

The following discussion of the prior art is intended to present the invention in an appropriate technical context and allows its significance to be properly appreciated. Unless clearly indicated to the contrary, reference to any prior art in this specification should not be construed as an expressed or implied admission that such art is widely known or forms part of common general knowledge in the field.

Sodium-glucose co-transporters inhibitors (SGLTs), such as SGLT1 and SGLT2 inhibitors provide new therapeutic targets to reduce hyperglycaemia in patients with diabetes. SGLT1 enables the small intestine to absorb glucose and contributes to the reabsorption of glucose filtered by the kidney. SGLT2 is responsible for reabsorption of most of the glucose filtered by the kidney, inhibitors with varying specificities for these transporters can slow the rate of intestinal glucose absorption and increase the renal elimination of glucose into the urine.

Sodium-glucose co-transporter 2 (SGLT2) inhibitors are a new class of diabetic medications indicated only for the treatment of type 2 diabetes. They have been studied alone and with other medications including metformin, sulfonylurea*, pioglitazone and insulin.

SGLT2 is a protein in humans that facilitates glucose reabsorption in the kidney. SGLT2 inhibitors block the reabsorption of glucose in the kidney, increase glucose excretion, and lower blood glucose levels.

Currently various SGLT2 inhibitor drugs have been approved or in clinical phase for treatment of type 2 diabetes, A significant numbers of SGLT2 are β-C-arylglueosides derived drug candidates, most of which comprises a central 1-deoxyglucose ring moiety that is arylated with different substitutions. Among β-C-aryiglucosides the pharmaceutically valuable drugs that are now being marketed are Canagliflozm (Formula I), Dapagliflozin (Formula II), Empagliflozin (Formula III), whereas Ipragliflozin (Formula IV) is approved for marketing in Japan. The structures of these compounds are as given below:

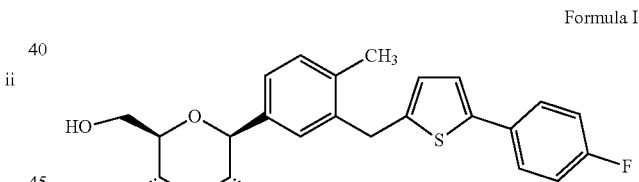

Formula I

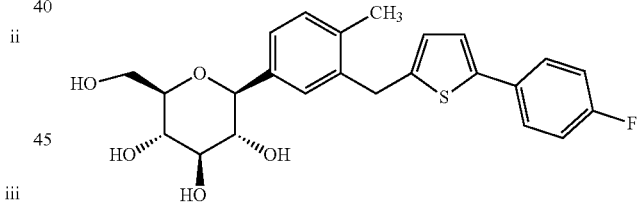

Formula II

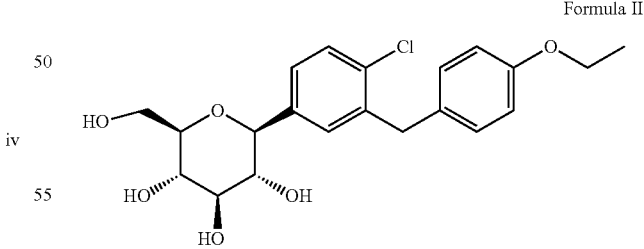

Formula III

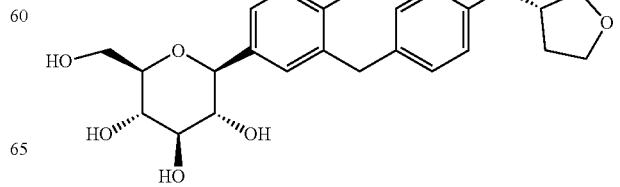

Formula IV

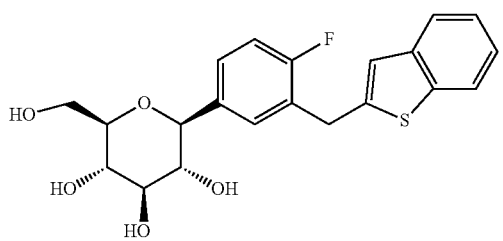

Formula X

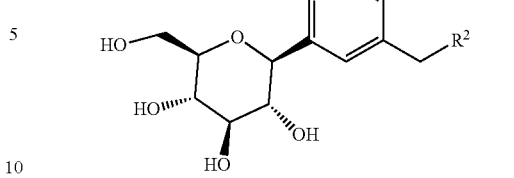

wherein, $R_1$ and $R_2$ are as defined above.

The principle object of the present invention is to provide an efficient process to prepare intermediates of SGLT2 inhibitors having good yield and high purity thereof.

The major object of the present invention is to provide an efficient process to prepare intermediates of SGLT2 inhibitors having optimized condition to give better reaction profile in terms of significantly reduced impurities and ultimately gives better yield and purity as compared to prior art.

Another important object of the present invention is to provide SGLT2 inhibitors in high purity, preferably >99%, more preferably >99.5%.

Another significant object of the present invention is to provide a process for the preparation of SGLT2 inhibitors involving less unit operations.

Another object of the present invention is to provide an in-situ process starting from compound of formula A to isolate substantially pare acetylated SGLT2 inhibitors.

There are various patents and patent applications viz., U.S. Pat. Nos. 6,515,117, 7,579,449, 7,772,407, 7,943,788, WO 2009035969, WO 2004063209, WO 2010022313, WO 2010043682, WO 2011047113, and WO 2013152476 which discloses the process for the preparation of these SGLT2 inhibitors. Most of these processes involve glucose or glucono lactone moiety for the preparation of the required compound.

In the prior art processes, hydroxyl group of the glucono-lactone moiety is protected with trimethylsilane. The process discloses the reaction where after the C—C bond formation the resultant hemiketal formed is methylated using methanesulphonic acid. During the process the trimethylsilyl groups are hydrolysed and get removed. The demethylation of the methoxy group and protection with acetyl group followed by de-acetylation to isolate the required compound.

Above described processes make use of drastic reaction conditions, more unit operations; additional purification by chromatography to get high enantiomeric and chemical purity which leads to loss of yield and that is not desirable for commercial manufacturing as well, as plant-scale point of view.

Existing processes are suffering from drawbacks like tedious processes, loss of yield, long reaction time cycle, more energy consumption, loss of human hours and involvement of more inventories as well as unit operations.

Inventors of the present invention have developed an improved process that addresses the problems associated with the processes reported in the prior art. The process of the present invention does not involve more unit operation. Moreover, the process does not require critical workup procedure. Accordingly, the present Invention provides a process for the preparation of SGLT2 inhibitors simple, efficient, cost effective, in reaction itself by designing optimum condition for reaction to reduce effluent load, environment friendly and commercially scalable for large scale operations.

SUMMARY OF THE INVENTION

In one aspect, the present invention relates to an improved process for the preparation of SGLT2 inhibitors.

In another aspect, the present invention relates to an improved process for the preparation of SGLT2 inhibitors resulted in good yield, preferably more than 70%.

In another aspect, the present invention relates to an improved process for the preparation of acetylated SGLT2 inhibitors, wherein acetylated SGLT2 inhibitors resulted in good overall yield, preferably more than 70%.

In another aspect, the present invention relates to an improved process for the preparation of SGLT2 inhibitors, wherein final compounds resulted in high purity, preferably >99.5%.

In another aspect, the present invention related to an improved process for the preparation, of SGLT2 inhibitor's, wherein the multi-step reaction in which condensation reaction, deprotection, reduction, protection to form acetylated SGLT2 inhibitors are conducted in-situ by telescopic monitoring of reaction.

In another aspect, the present invention relates to a process for the preparation of acetylated SGLT2 inhibitors, wherein purifying formed acetylated SGLT2 inhibitors by treating with suitable, solvents or mixture of solvents to obtain acetylated SGLT2 inhibitors having purity greater than 99%.

OBJECT OF THE INVENTION

The primary object of the present invention is to provide a robust and cost effective process for the preparation of sodium glucose transporters 2 (SGLT2) compound of Formula X,

DETAILED DESCRIPTION OF THE INVENTION

In the context of the present invention, the term "mixture" means that the mixture of solvents in any suitable ratio. All alternatives are intended to be within the scope, of the present invention.

All ranges recited herein include the endpoints, including those that recite a range "between" two values. Terms such as "about", "generally" and the like are to be construed as modifying a term or value such that it is not an absolute. Such terms will be defined by the circumstances and the terms that they modify as those terms are understood, by those skilled in the art. This includes, at very least, the degree of expected experimental error, technique error and instrument error for a given technique used to measure a value.

The term: "in-situ" typically means "in the reaction mixture" or "not in isolated form" or "existing as residue".

Accordingly, in an embodiment the present invention relates to an improved process for the preparation of SGLT2 inhibitors represented by the following formula X and its hydrates, solvates or salts thereof,

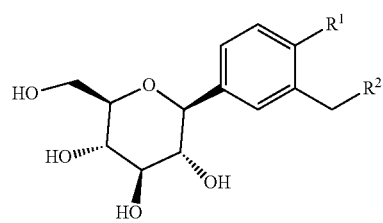

Formula X wherein, $R_1$ and $R_2$ are as defined above,
comprising following steps;
a) reacting the compound of formula A with, the compound of formula B in suitable solvent in the presence of organolithium reagent to provide the compound of formula C;

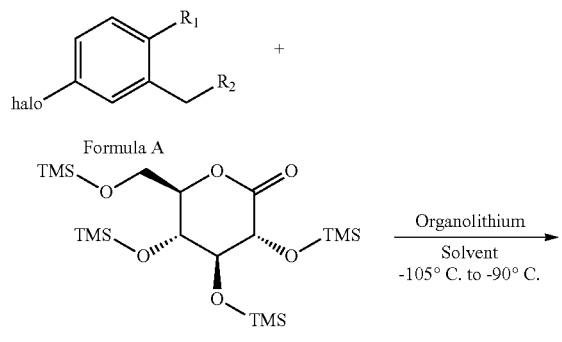

Formula A

Formula B

Formula C b) reacting the compound of formula C with methanesulphonic acid in suitable solvent in to provide the compound of formula D;

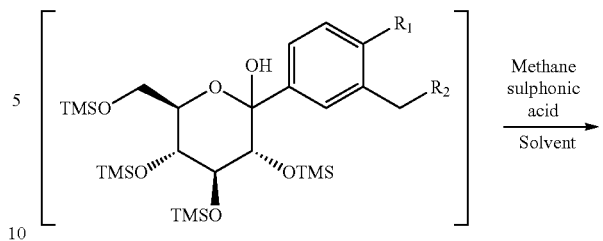

Formula C

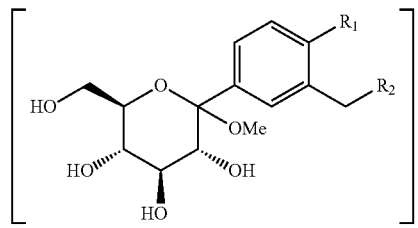

Formula D c) reacting the compound of formula D with reducing agent in suitable solvent to form the compound of formula E;

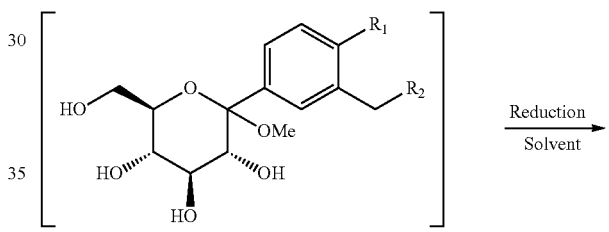

Formula D

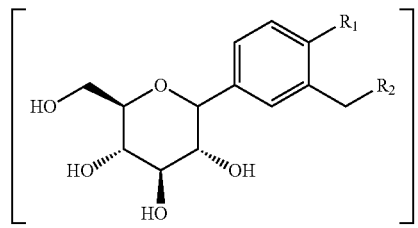

Formula E d) acetylating the compound of formula E in the presence of acetylation agent in suitable solvent to isolate compound of formula F,

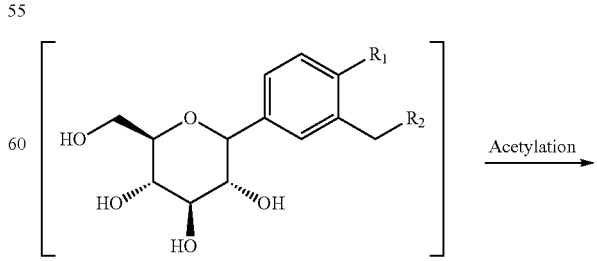

Formula E

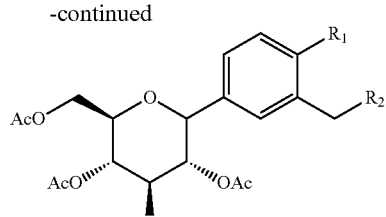

Formula F e) hydrolyzing compound of formula F in the presence of base in suitable solvent to form SGLT2 inhibitors of formula X; and
f) optionally converting SGLT2 inhibitors of formula X into its hydrates, solvates or salts thereof,
wherein the compounds of formula C, D and E are formed in-situ.

In an embodiment, the suitable solvent used in the process herein above is selected from the group comprising of water, alcohols, ethers, amides, esters, nitriles, sulfoxides, ketones, hydrocarbons and halogenated hydrocarbons; wherein alcohol Is selected from the group consisting of methanol, ethanol, iso-propanol, n-butanol, iso-butanol and the like; ester is selected from the group consisting of ethyl acetate, isopropyl acetate; ketone is selected from the group consisting of acetone, methyl isobutyl ketone, methyl ethyl ketone; ether is selected from the group consisting of methyl tert-butyl ether, diisopropyl ether, diethyl ether tetrahydrofuran, 2-methyl tetrahydrofuran, cyclopentyl methyl ether, dioxane and the like; halogenated solvent Is selected from the group consisting of dichloromethane, chloroform, chlorobenzene, bromobenzene and the like; hydrocarbons is selected from the group consisting of toluene, xylene, cyclohexane and the like; nitrile is selected from the group consisting of acetonitrile, propionitrile and the like; amide is selected from the group consisting of N,N-dimethylformamide, N,N-dimethyl acetamide and the like; sulfoxide such as dimethyl, sulfoxide; sulfone; or mixtures thereof.

In an embodiment, organolithium reagent may be selected from n-butyllithium, sec-butyllithium, isopropyllithium, tert-butyllithium and the like.

In an embodiment, reducing agent may be mixture of diethyl silane and aluminum chloride.

In an embodiment, acetylation reagent may be selected from acetic anhydride or acetyl chloride.

In an embodiment, base may be selected trim inorganic base or organic base or mixtures thereof.

In an embodiment, the organic base is selected front the group consisting of 1,8-diazabicyclo[5,4,0]undec-7-ene (DBU), 1,5-diazabicyclo[4,3,0]non-5-ene (DBN), pyridine, dimethylaminopyridine, dibutyl amine, triethyl amine, tributyl amine, diisopropyl amine, diisopropylethylamine, N-methylmorpholine and the like.

In an embodiment, the inorganic base is selected front the group consisting of hydroxides of alkali metals or alkaline earth metals such as sodium hydroxide, potassium hydroxide, lithium hydroxide, calcium hydroxide; carbonates such as sodium carbonate, potassium carbonate; bicarbonates of alkali metals or alkaline earth metals such as sodium bicarbonate, potassium bicarbonate; ammonia and the like.

The main objective of the present invention is to achieve high purity and yield, simultaneously avoiding use of $BF_3$-etherate as reducing agent which always requires safety precautions. Moreover that, recovery of compound of formula X via the in-situ transformation from compound of formula A increases overall yield from 46% to 57% as compared to prior art.

Accordingly, in an embodiment the present, invention relates to an improved process for the preparation of acetylated SGLT2 inhibitors of formula F,

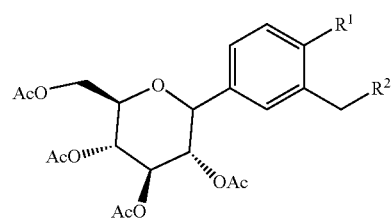

Formula F wherein, $R_1$ and $R_2$ are as defined above,
comprising following steps;
a) reacting the compound of formula A with the compound of formula. 8 in suitable solvent in the presence of organolithium reagent to provide the compound, of formula C;

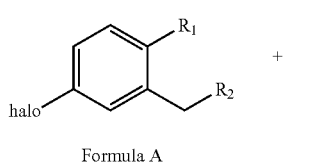

Formula A

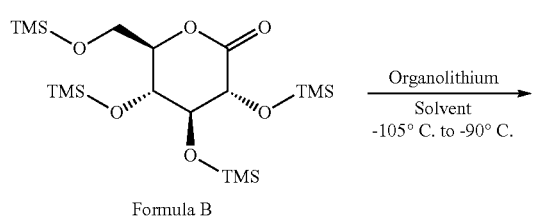

Formula B

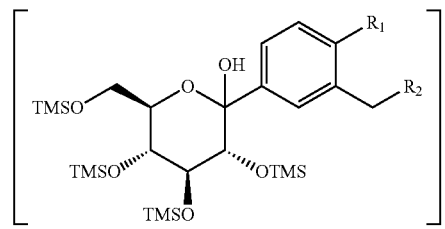

Formula C b) reacting the compound of formula C with methanesulphonic acid in suitable solvent to provide the compound of formula D;

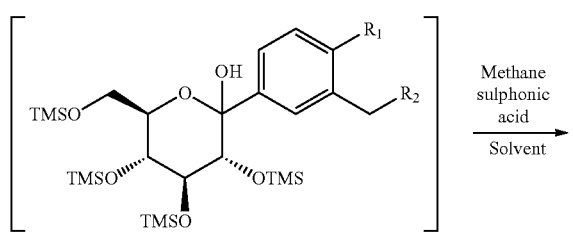

Formula C

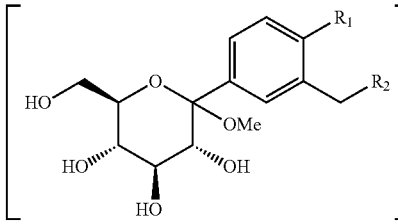

Formula D c) reacting the compound of formula D with reducing agent in suitable solvent to form the compound of formula E;

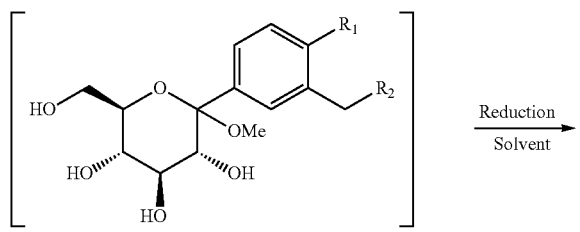

Formula D

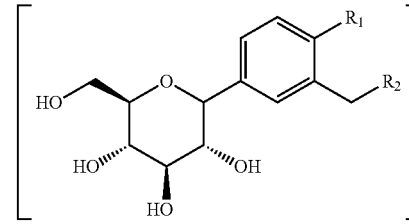

Formula E d) acetylating the compound of formula E in the presence of acetylation agent in suitable solvent to isolate compound of formula F,

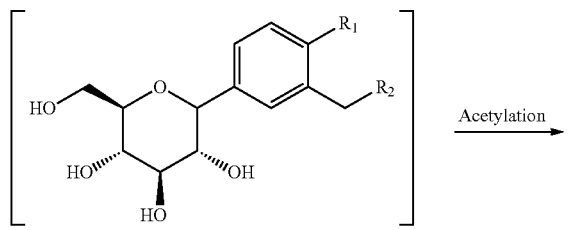

Formula E

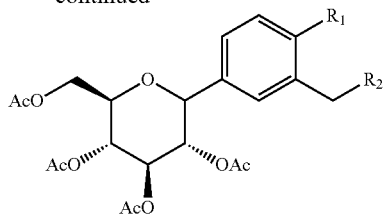

Formula F wherein the compounds of formula C, D and E are formed in-situ.

In an embodiment, the suitable solvent used in the process herein above is selected from the group comprising of water, alcohols, ethers, amides, esters, nitriles, sulfoxides, ketones, hydrocarbons and halogenated hydrocarbons; wherein alcohol is selected from the group consisting of methanol, ethanol, iso-propanol, n-butanol, iso-butanol and the like; ester is selected from the group consisting of ethyl acetate, isopropyl acetate; ketone is selected from the group consisting of acetone, methyl isobutyl ketone, methyl ethyl ketone; ether is selected from the group consisting of methyl tert-butyl ether, diisopropyl ether, diethyl ether tetrahydrofuran, 2-methyl tetrahydrofuran, cyclopentyl methyl ether, dioxane and the like; halogenated solvent is selected from the group consisting of dichloromethane, chloroform, chlorobenzene, bromobenzene and the like; hydrocarbons is selected from the group consisting of toluene, xylene, cyclohexane and the like; nitrile is selected from the group consisting of acetonitrile, propionitrile and the like; amide is selected from the group consisting of N,N-dimethylformamide, N,N-dimethyl acetamide and the like; sulfoxide such as dimethyl sulfoxide; sulfone; or mixtures thereof.

In an embodiment, organolithium reagent may be selected from n-butyllithium, sec-butyllithium, isopropyllithium, tert-butyllithium and the like.

In an embodiment, reducing agent may be mixture of triethylsilane and aluminum chloride.

In an embodiment, acetylating reagent may be selected from acetic anhydride or acetyl chloride.

In an embodiment, base may be selected from inorganic base or organic base or mixtures thereof.

In an embodiment, the organic base is selected from the group consisting of 1,8-diazabicyclo[5.4.0]undec-7-ene (DBU), 1,5-diazabicyclo[4.3.0]non-5-ene (DBM), pyridine, dimethylaminopyridine, dibutyl amine, triethyl amine, tributyl amine, diisopropyl amine, diisopropylethylamine, N-methylmorpholine and the like.

In an embodiment, the inorganic base is selected from the group consisting of hydroxides of alkali metals or alkaline earth metals such as sodium hydroxide, potassium hydroxide, lithium hydroxide, calcium hydroxide; carbonates such as sodium carbonate, potassium carbonate; bicarbonates of alkali metals or alkaline earth metals such as sodium bicarbonate, potassium bicarbonate; ammonia and the like.

Accordingly, in an embodiment the present invention relates to a process for the preparation of compound of formula C, comprising the step of: reacting the compound of formula A with the compound of formula B in suitable solvent in the presence of organolithium reagent to provide the compound of formula C, wherein reaction preferably conducted at the temperature −105° C. to −90° C.

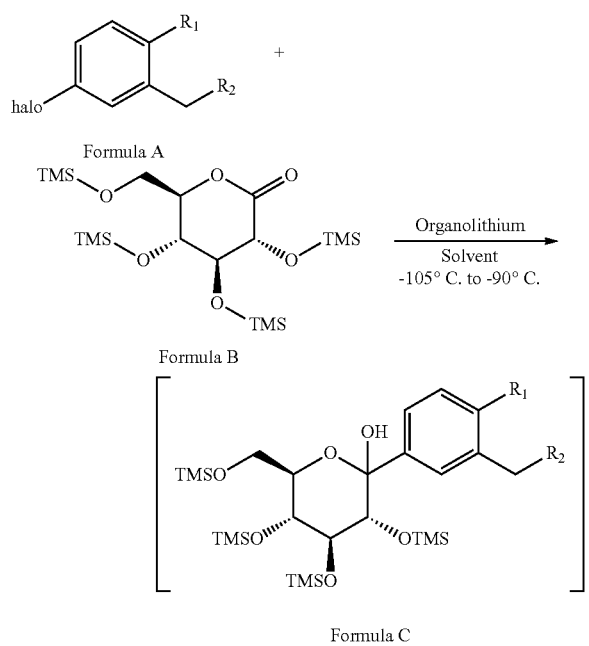

Surprisingly, it has been found that, in the preparation of compound of formula C, the reaction temperature has critical role, which gives better reaction profile in terms of significantly reduced impurities such as dimer impurity and ultimately gives better yield and purity as compared to prior art.

Accordingly, in an embodiment the present invention relates to a process for the preparation of acetylated SGLT2 inhibitors of formula F, wherein purifying formed acetylated SGLT2 inhibitors by treating with halogenated solvent and/or alcohol or mixtures thereof yields acetylated SGLT2 inhibitors of formula F having purity greater than 99%.

In an embodiment, the suitable solvent used in the process herein above is selected from the group comprising of water, alcohols, halogenated hydrocarbons; or mixtures thereof, wherein alcohol is selected from the group consisting of methanol, ethanol, iso-propanol, n-butanol, iso-butanol and the like; halogenated solvent is selected from the group consisting of dichloromethane, chloroform, chlorobenzene, bromobenzene and the like.

The significant advantages of the present invention is to provide purer compound of formula F by treating with halogenated solvent and/or alcohol or mixtures thereof to control the impurities below 0.1%. Hence there is no specific purification requirement of final SGLT2 inhibitors of formula X as impurities can be controlled at formation of compound of formula F.

Accordingly, in an embodiment the present invention relates to a process for the preparation of SGLT2 inhibitors of formula X, wherein purifying formed SGLT2 inhibitors by treating with suitable solvent or mixture of solvents or by crystallization or by solvent—antisolvent treatment to provide SGLT2 inhibitors of formula X having purity greater than 99%.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present, invention.

EXAMPLES

Example-1; Preparation of Acetylated Canagliflozin (Formula F)

2-(5-iodo-2-Methylbenzoyl)-5-(4-fluorophenyl) thiophene (100 gm) and 2, 3, 4, 6-tetra-O-trimethylsilyl-β-D-glucolactone (148.8 g) were dissolved in tetrahydrofuran (700 ml) and cooled to −100° C. to −90° C. To the obtained reaction mixture n-BuLi (156.3 g, 1.6 M) in hexane was added at a temperature maintained below 90° C. The solution was stirred till completion of reaction at −95° C. before to quenching by methanol and acidified with methanesulfonic acid. The reaction mass was stirred till completion of reaction at 25° C. to 35° C. The reaction, once completed as indicated by HPLC analysis, was quenched by the addition of trimethylamine. To this was added water (500 mL) and extracted twice with dichloromethane. The combined dichloromethane layers were washed with brine solution. This organic layer containing O-methoxy intermediate was added to the mixture of triethylsilane (71.3 gm) and aluminum chloride (98.0 gm) in 0.1:1 ratio of acetonitrile and dichloromethane mixture at 0° C. to 5° C. Further this reaction was quenched by using 10% aqueous hydrochloric acid solution and the product was extracted using dichloromethane and washed with brine solution. This organic layer was dried over sodium sulphate. After the sodium sulphate is filtered, the organic layer was washed with dichloromethane and transferred to an assembly. To this acetic anhydride (225 gm), DMAP (3.0 gm) as catalyst and pyridine (3.0 gm) were added and stirred for 12-14 h at 25-35° C. Further this reaction mixture was quenched using water and extracted using dichloromethane. The organic layer containing acetylated canagliflozin was concentrated under vacuum at 40-45° C. The crude acetylated canagliflozin was Isolated using isopropyl alcohol by heating the crude oil in Isopropyl alcohol at 75-80° C. to get white to yellow slurry and gradually cooled to 2535° C. over the period of 6-7 h. This was then filtrated at 25-35° C. and washed with isopropyl alcohol to give acetylated canagliflozin. The acetylated canagliflozin is further purified in methylene chloride and isopropyl alcohol (1:5) at 40-45° C. followed by the filtration at 25-35° C. and drying under vacuum at 60-65° C. to obtain acetylated canagliflozin.
Yield: 57%
Purity (by HPLC): ≥99.8%

Example-2: Preparation of Canagliflozin Hemihydrate (Formula X)

To the solution of methanol (250 mL), water (25 mL) and sodium hydroxide (14.7 gm), acetylated canagliflozin was added at temperature 25-35° C. The reaction mixture was flushed with methanol (50 mL) and stirred for 0.10-15 minutes followed by maintaining the reaction mixture at 60-70° C. for 2 hours. The reaction mixture was then cooled to 25-35° C. and acetic acid (5 mL) was added into it at 25-35° C. to adjust the pH 6.5-8.0. Isopropyl acetate (250 mL) and water (300 mL) were added into the reaction mixture at temperature 25-35° C. and stirred for 15-20 minutes followed lay separating the layers. Aqueous layer was extracted twice with Isopropyl acetate (100 mL). The organic layer was washed with demineralized (DM) water (250 mL) followed by charcoal treatment. The solvent was distilled under vacuum at below 55° C. up to 2.5 to 3.5 volumes. The reaction mixture was then cooled to 25-35° C. and water (15 mL) was added and stirred 25-30° C. for 30-45 minutes. The reaction mixture was then added cyclohexane (250 mL) at 25-30° C. and stirred at 2530° C. for 12-15 hours. The product was littered under vacuum at 25-30*0 and washed the product with cyclohexane (100 mL) and dried the material under vacuum 50-55° C. till water and residual solvents comes under limit to obtain Canagliflozin hemihydrate,
Yield: ~90%
Purity (by HPLC): ≥99.9%

Example-3: Preparation of Canagliflozin Hemihydrate (Formula X)

To the solution of methanol (250 mL), water (25 mL) and sodium hydroxide (14.7 gm), acetylated canagliflozin was added at temperature 23-35° C., The reaction mixture was flushed with methanol (50 mL) and stirred for 10-15 minutes followed by maintaining the reaction mixture at 60-70° C. for 2 hours. The reaction, mixture was then, cooled to 25-35° C. and acetic acid (5 mL) was added into it at 25-35° C. to adjust the pH 6.5-8.0. Dichloromethane (250 mL) and water (300 mL) were added into the reaction mixture at temperature 25-35° C. and stirred for 15-20 minutes followed by separating the layers. Aqueous layer was extracted twice with dichloromethane (100 mL). The organic layer was washed with DM water (250 mL) followed by charcoal treatment. The solvent was distilled under vacuum completely. Toluene (250 mL) was added into the residue. The reaction mixture was then cooled to 25-35° C. and water (15 mL) was added and stirred 25-30° C. for 30-45 minutes. The reaction mixture was then added cyclohexane (250 mL) at 25-30° C. and stirred at 25-30° C. for 12-15 hours. The product was filtered under vacuum at 25-30° C. and washed the product with cyclohexane (100 mL) and dried the material under vacuum 50-55° C. till water and residual solvents comes under limit to provide Canagliflozin hemihydrate.
Yield: ~90%
Purity (by HPLC): ≥99.9%

Example-4: Preparation of Acetylated Empagliflozin (Formula F)

To the solution of (S)-3-(4-(5-bromo-2-chlorobenzyl))phenoxy)tetrahydrofuran in tetrahydrofuran n-BuLi (2.5 mol) in hexane added at a rate that maintained the reaction temperature below −90° C. followed by addition of 2,3,4,6-tetra-O-trimethylsilyl-β-D-glucolactone in toluene at a rate that maintained the reaction temperature below −90° C. The solution was stirred for 30 ruin at −95° C. prior to quenching by addition of methanol containing methanesulfonic acid. The reaction mixture was stirred overnight as the temperature raise to 20° C. After completion of reaction, the reaction was quenched by the addition of triethylamine and distilled it out under vacuum. To the obtained residue water was added and extracted thrice with ethylacetate. The combined ethylacetate fractions were washed with brine and dried over sodium sulfate. The reaction mixture was concentrated to provide formula C in the form oil. To the methylenechloride solvent, aluminum chloride was added in one lot and cooled the mass to the temperature 0° C. to 10° C. To the prepared solution acetonitrile was added followed by addition of triethyl silane at a rate such that the temperature was maintained between 0° C. to 10° C. Mixed the above prepared complex with oil of formula C and stirred for 2 h. When HPLC analysis revealed that the reaction was completed, the reaction was quenched by addition of 50% aqueous hydrochloric acid solution. Aqueous layer was extracted with methylenechloride. Combined organic layer washed with 5% aqueous hydrochloric acid solution followed by water and brine. The organic layer was distilled and the obtained residue was added methylenechloride, acetic anhydride and dimethylaminopyridine, pyridine and stirred for 5-6 h. Water was added to the reaction mixture and layers were separated. The methylenechloride layer was distilled and ethanol was added to it followed by heating to 55-60° C. The reaction mixture was cooled, filtered and dried, to obtain acetylated empagliflozin of formula F.
Yield: ~58%
Purity (by HPLC): ≥99.8%

We claim:
1. A process for the preparation of SGLT2 inhibitor compound (X) or a hydrate, solvate or salt thereof,

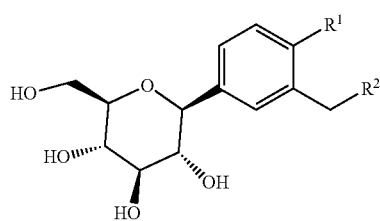

Formula X wherein, $R_1$ is halogen, alkyl or alkoxy group; and
$R_2$ is aryl group or heterocyclic ring selected from the group of i, ii, iii or iv as shown below

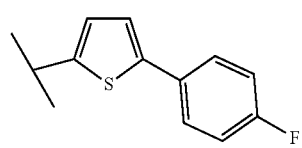

i

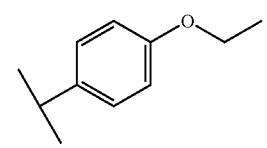

ii

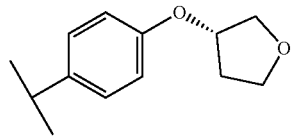

iii

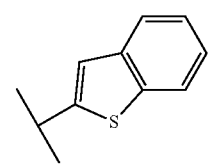

iv the process comprising the steps of;
a) reacting compound of formula A with compound of formula B in a solvent at temperature ranging between −105° C. to −90° C. in presence of organolithium reagent selected from the group consisting of n-butyllithium, sec-butyllithium, isopropyllithium and tert-butyllithium, to provide compound of formula C;

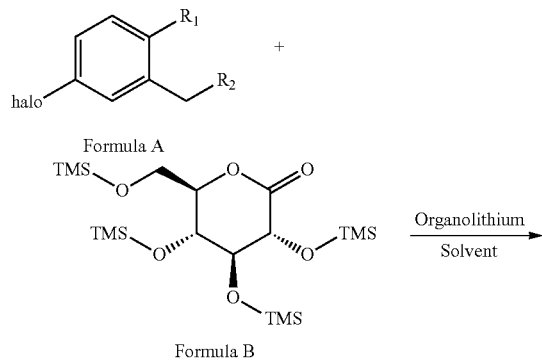

Formula A

Formula B b) reacting the compound of formula C with methanesulphonic acid in a solvent to provide compound of formula D;

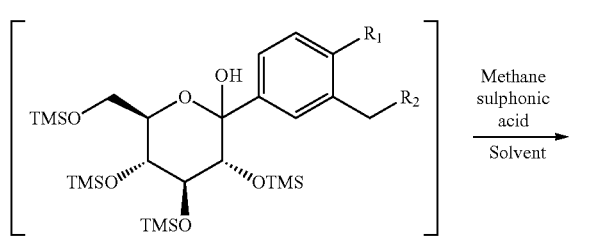

Formula C

Formula D c) reacting the compound of formula D with reducing agent, which is a mixture of triethylsilane and aluminum chloride, in a solvent to form compound of formula E;

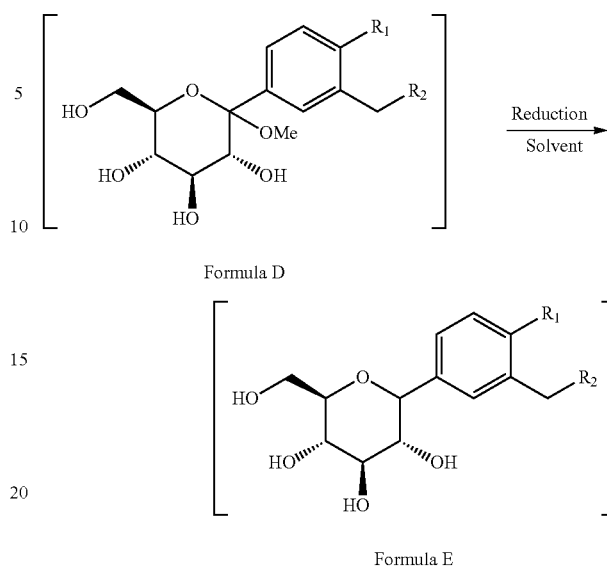

Formula D

Formula E d) acetylating the compound of formula E in the presence of acetylating reagent selected from the group consisting of acetic anhydride and acetyl chloride, in a solvent to isolate compound of formula F;

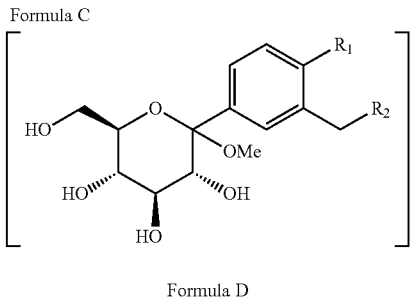

Formula E

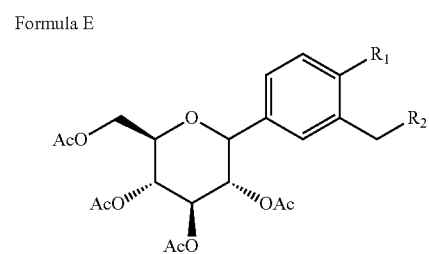

Formula F e) hydrolyzing compound of formula F in presence of base in a solvent to a form SGLT2 inhibitor of formula X; and f) optionally converting SGLT2 inhibitor of formula X into a hydrate, solvate or salt thereof;

wherein compounds of formula C, D and E are formed in-situ.

2. The process according to claim 1, wherein the compound of formula F is treated with halogenated solvent, alcohol solvent water or a combination thereof, to yield pure compound of formula F having impurities less than 0.1;

Formula F

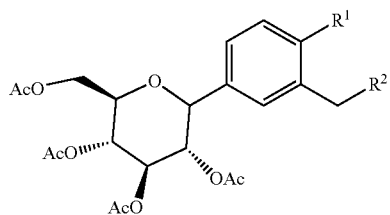

wherein, R₁ is halogen, alkyl or alkoxy group and R₂ is aryl group Or heterocyclic ring selected from the group of i, ii, iii or iv as shown below:

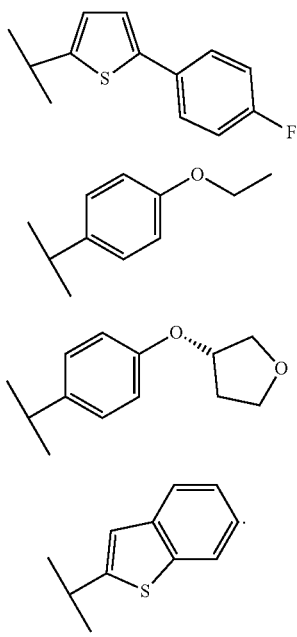

treating with aromatic hydrocarbon solvent, aliphatic hydrocarbon solvent, water, or a combination thereof; to obtain pure SGLT2 inhibitor compound (X)

FORMULA X

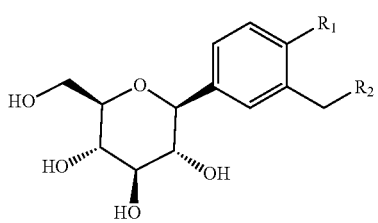

wherein, R₁ is halogen, alkyl or alkoxy group and R₂ is aryl group or heterocyclic ring selected from the group of i, ii, iii or iv as shown below:

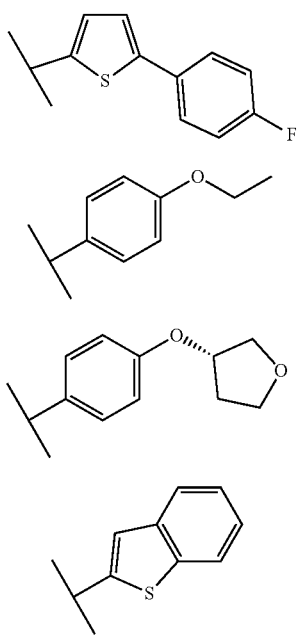

having purity greater than 99%.

3. The process according to claim 2, wherein the obtained product is pure acetylated compound of formula F having purity greater than 99%.

4. The process according to claim 2, wherein the solvent is selected from the group comprising of water, alcohols, halogenated hydrocarbons; or mixtures thereof, wherein alcohol is selected from the group consisting of methanol, ethanol, iso-propanol, n-butanol and iso-butanol; and halogenated solvent is selected from the group consisting of dichloromethane, chloroform, chlorobenzene and bromobenzene.

5. The process according to claim 1, wherein the SGLT2 inhibitor compound (X) obtained in step (e) is purified by 6. The process according to claim 5, wherein the aromatic hydrocarbon solvent is selected from the group consisting of toluene and xylene; and aliphatic hydrocarbon solvent is selected from the group consisting of cyclohexane and n-hexane.

\* \* \* \* \*